United States Patent [19]

Dybdahl

[11] Patent Number: 5,538,689
[45] Date of Patent: Jul. 23, 1996

[54] LIQUID SAMPLE ANALYSER

[76] Inventor: Bjørn Dybdahl, Lillesund Terrasse 4D, N-5500 Haugesund, Norway

[21] Appl. No.: 257,924
[22] PCT Filed: Aug. 6, 1992
[86] PCT No.: PCT/NO92/00127
 § 371 Date: Feb. 10, 1994
 § 102(e) Date: Feb. 10, 1994
[87] PCT Pub. No.: WO93/04366
 PCT Pub. Date: Mar. 4, 1993

[30] Foreign Application Priority Data

Aug. 15, 1991 [NO] Norway .................................... 913182

[51] Int. Cl.⁶ .................................................. G01N 30/20
[52] U.S. Cl. ............................ 422/70; 422/81; 436/161; 210/638
[58] Field of Search .................... 422/70, 81, 82; 210/638, 656, 149, 294; 436/161

[56] References Cited

U.S. PATENT DOCUMENTS

| | | | |
|---|---|---|---|
| 3,860,393 | 1/1975 | Campen, Jr. ......................... | 436/161 X |
| 4,472,354 | 9/1984 | Passell et al. ....................... | 436/161 X |
| 4,981,804 | 1/1991 | Hanaoka et al. .................... | 436/161 X |
| 5,417,853 | 5/1995 | Mizuno et al. ...................... | 436/161 X |

OTHER PUBLICATIONS

"Instrumental Methods of Analysis" 6th ed., California, Wadsworth Publishing Company, 1981 pp. 495–496.

*Primary Examiner*—Jeffrey R. Snay
*Attorney, Agent, or Firm*—Fulbright & Jaworski

[57] ABSTRACT

The invention relates to a liquid sample analyzer for analyzing water samples for metal or other element content. The measurement can be made simultaneously with the determination of electrical conductivity and/or degree of acidity. The invention includes at least two mobile phase containers, and each of the mobile phase containers contains a different reagent. In addition there are elements for causing each of the different reagents to flow from the mobile phase containers to separate pipelines. The pipelines are connected to injection valves which inject the different reagents into a pipeline together with a common liquid sample. The mixed sample and reagent are then introduced into an ion separating column. The invention further is comprised of a detector for detecting data from said ion separating columns, a recorder for recording said detected data, and a casing to enclose the valves and ion separating columns. Determination of all the liquid sample parameters are achieved under the same conditions, i.e. temperature and pressure, and only a single injection of sample liquid is required. Other sensor devices, for example devices for measuring conductivity or pH, may be added to the analyzer.

4 Claims, 1 Drawing Sheet

LIQUID SAMPLE ANALYSER

FIELD OF THE INVENTION

The invention relates to a liquid sample analyser, in particular an ion analyser for water samples to use for determining the content of metals and other elements, such as chlorides, sulphates etc as well as the conductivity and pH of water samples.

The purpose of any test carried out using such a liquid sample analyser is to determine the water quality of for example, water from a seabed formation or, for example, waste water from a treatment plant.

BACKGROUND OF THE INVENTION

By introducing injection liquid into a seabed formation, one is able, with the said liquid sample test, to choose the correct chemicals for blending with the injection water. If the injection water is not treated with the correct chemicals in the correct amount, the seawater within the seabed formation will react negatively with the injection liquid and form undesired salts etc. which are liable to clog bore holes and channels within the formation and thus seal them when the injection water is introduced from the surface.

Such liquid sample analysers are known as eleven-ion analysers, wherein a liquid sample is analysed with regard to eleven distinct parameters, e.g. content of sodium, potassium, magnesium, bivalent iron, calsium, strontium, barium, chlorides and sulphate, as well as the pH-value and electrical conductivity.

With this invention, the number of parameters is not restricted to precisely eleven; the parameter number may be greater or smaller. Thus, an eleven-ion analyser constitutes only one aspect of the invention.

There are no apparatus or instruments available on the market today which allow the determination of the above-mentioned element contents, chloride and sulphate contents, as well as the level of acidity and electrical conductivity, by means of one system based on a liquid sample injection and which allows analysis of all parameters under the same conditions (pressure/temperature).

For liquid sample analysis of the kind described above, the following known apparatus are used at present:

One system presently available is based on atomic absorption spectrophotometry, and another system is based on inductive plasma technique. Both comprise bulky, heavy instruments capable of analysing only some of the elements included in an eleven-ion analysis.

For each of these available instruments, a pH measuring device, a conductivity metering apparatus, an ion chromatograph or ion-selective electrodes or a spectrophotometer must be used as additional equipment. There is also the disadvantage with these techniques that the liquid samples have to be transported from the water source (which can sometimes be located far away) to a laboratory.

If one uses an analysis procedure based on the above-mentioned atomic absorption, the liquid sample has to be diluted in order to reduce the-concentration parameter to 1/1000 (one part per thousand). Such a dilution gives rise to substantial margins of error, and if, for example, 1000 tests were performed on this basis, the results might substantially very. Tests in such a number are performed routinely with the above-mentioned seawater or formation water analysis.

Therefore, one the present invention one has primarily aimed at eliminating or substantially reducing the difficiences, disadvantages and limitations in the available technique. This will provide a liquid sample analyser which achieves more accurate measurements. The conditions are optimized in order to obtain an accurate determination of, for example, the above-mentioned eleven parameters by means of a single system consisting of assembled components, on the basis of one single sample liquid injection, and where all the said parameters (more/less) are analysed under the same conditions.

The liquid sample analyser according to the invention, which is based on ion chromatography, is designed as a portable unit made up of easily assembled portable components, so that the analyser may be used in situ, i.e., the system can be installed at the source of the water to be analysed.

According to the invention, the above-mentioned aims are achieved by designing a liquid analyser in such a way that it demonstrates the features defined in the following claims.

Since the liquid analyser is based on ionchromatography, it is capable of treating and analysing undiluted liquid samples, thus avoiding the above-mentioned sources of error. An ion chromatograph determines which ions are present in a liquid sample as well as the consentrations of these ions.

DETAILED DESCRIPTION OF THE INVENTION

Figure 1:
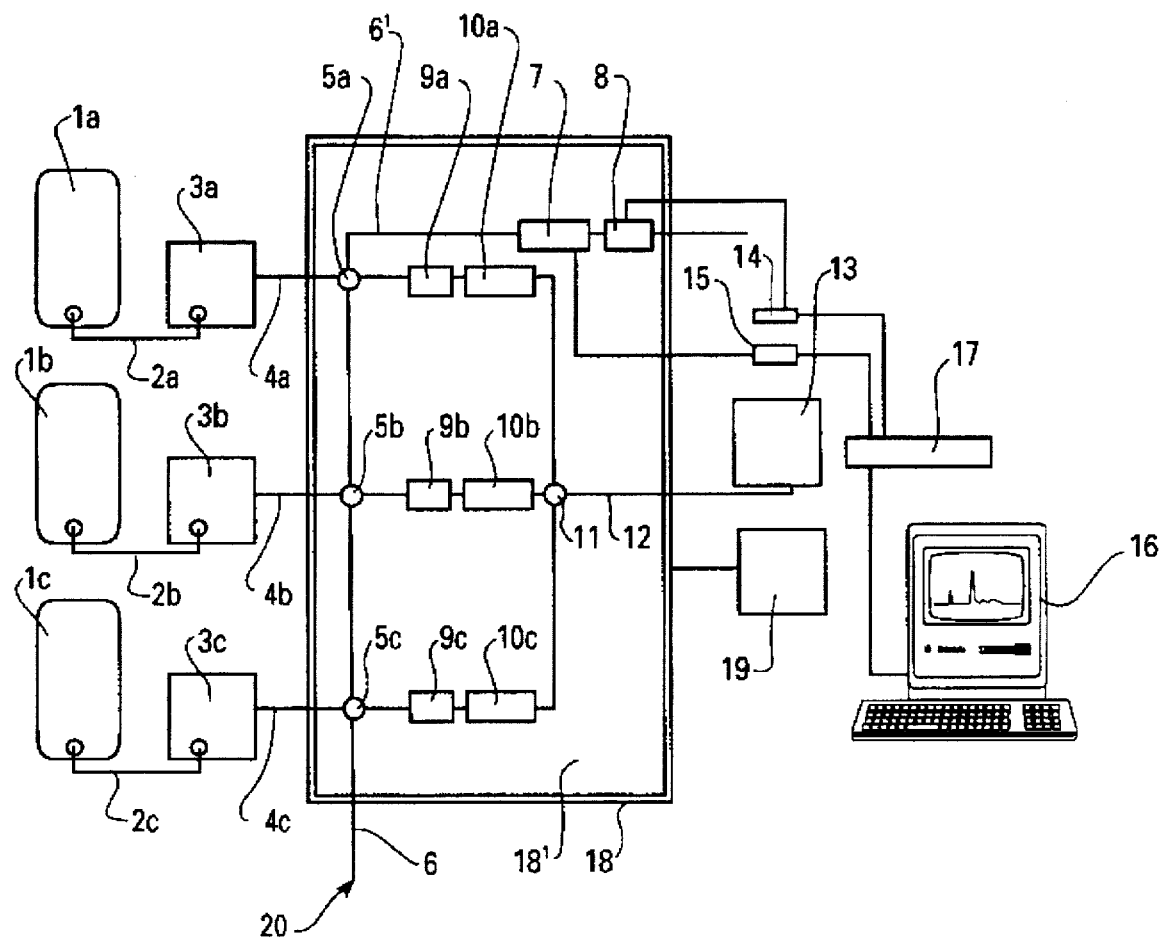
FIG. 1 shows a schematic flow/circuit diagram of some of the components of the portable liquid sample analyser of the present invention.

The liquid sample chromatograph comprises separator columns where the ions are separated depending on the electrical charge of the column. The stationary phase of such a column for anions is positively charged, whilst the stationary phase of a column for cations is negatively charged. If the analyser, according to the invention, uses three such separator columns, a first column can be used for anions, a second column for monovalent cations and a third column for divalent cations. In connection with said three separator columns, three so-called mobile phase containers are used, each of the latter contains a reagent of its own. These reagents differ from each other, but are blended with the same liquid sample which is added to each single reagent simultaneously in one valve zone for each mobile phase container, situated between the latter and the associated separator column.

In a liquid sample analyser, according to the invention, only a single liquid sample injection into the system is required. In the above-mentioned embodiment which has three mobile phase containers each having an associated separator column, said valve zones form junction points with the supply pipeline for the liquid sample. In each of said valve zones, an identical amount of liquid sample is simultaneously separated. Thereby, the analyser is able to perform simultaneous measurement of eleven parameters or more/less than eleven parameters, respectively.

Since the liquid sample supply points (valves), the separator columns, and the measuring apparatus are enclosed within a common cabinet or furnace casing, the analysis will be conducted under the same conditions (pressure/temperature), which is essential for the achievement of accurate measuring, resulting in a higher quality of the total analysis result. The conditions have been adjusted for direct data analysis and logging, automatic sampling at distinct time intervals and transfer of data directly to control room via monitoring station to participant.

Moreover, a liquid sample analyser according to the invention, comprises a number of known components, i.e. an acidity metering device and conductivity measuring apparatus. The electrical conductivity of a liquid is closely related to the content of common salt, and the conductivity measuring apparatus is, in this case, used to indicate the common salt content in the liquid sample.

The reagents representing the mobile phase of the system are allowed to circulate continuously through the pipeline circuit of the apparatus, through the valves, separator columns and measuring instrument in a constant flow. Each separate reagent in the adjacent valve zone carries with it a distinctly measured amount of liquid sample into the separator zone and from there to the connected measuring instruments. All these steps take place within said cabinet or furnace casing enclosing the appurtenant system components, thereby enabling the maintenance of equal pressure/temperature conditions during the liquid sample supply/separating/measuring. Thus, the liquid sample becomes separated into its individual constituents, and arrives in this condition at the detector unit of the system, which records for example the content of chloride, magnesium etc. These recorded measurements are transferred to a computer via an analog/digital-converter in order to provide a hard copy.

The various reagents representing the mobile phase of the system are preferably water-based and exhibit the highest degree of purity possible.

A portable liquid sample analyser designed with a thermostat-controlled cabinet, wherein all analysis and separations take place, is illustrated as a non-restricting examplary embodiment in the accompanying drawing, wherein the single figure in block-diagrammatical form shows a schematic flow/circuit diagram of the most significant components of the analyser in assembled state.

In the figure of the drawing, the reference indications 1a, 1b, 1c denote three so-called mobile phase containers, each containing a separate reagent of its own. The reagents constitute mutually differing reaction participants for a liquid sample to be analysed.

Preferably, each single reagent is water-based and appears in an optimal state of purity.

Each mobile phase container 1a, 1b, 1c is via a pipeline 2a, 2b and 2c, respectively, in fluid communication with an associated pump 3a, 3b and 3c, respectively, each of which by means of an individual pipe line 4a, 4b and 4c, respectively, is connected to a liquid sample injection valve 5a, 5b and 5c, respectively.

The liquid injection valves 5a–5c form junction points with a liquid sample injection pipeline 6, through which the direction of flow is from the bottom upward according to the figure of the drawing and which, with an upper pipe line portion 6' (downstream of the upper/last injection valve 5a), is connected to a conductivity measuring apparatus 7 and an acidity metering device (pH-electrode) 8. There is later a description of an embodiment of the injection valves 5a–5c which enables an accurately-measured predetermined amount of liquid sample to be admitted into the circuit of each mobile phase reagent agent.

Each liquid sample injection valve 5a–5c is via a preseparator column 9a–9c connected to a main separator column 10a–10c. Downstream, the columns 10a–10c are joined at a junction point wherein a valve 11 has been placed, and from where a pipeline 12 leads to a detector unit 13, into which liquid samples, —blended into respective reagent—enter in separated state, i.e., first as chlorides, thereafter, as magnesium, etc.

The actual pH-metering device which is connected to the pH-electrode 9, is denoted by reference numeral 14; 15 indicating a conductivity regulator connected to the conductivity measuring apparatus 7. These instruments are commonly known and generally in use for water sample analysis.

Likewise, the components 13–15 are, as known per se, connected to a computer 16 via a data acquisition unit 17 having an analog/digital-converter.

The valve 11 is adapted to control the liquid sample/reagent-mixture from each single column 10a–10c to the detector 13.

In order to adjust the conditions for simultaneous measurement of all desired parameters during the same conditions in accordance with the invention, all liquid sample supplies (at 5a–5c) to the analyser, all ion separations (mainly at 10a–10c) as well as conductivity and pH-value meterings (within 7 and 8) within the analyser occur under exactly the same conditions (pressure/temperature).

In accordance with the invention, this is realised through enclosing the corresponding parts of the system into a cabinet or furnace casing, represented by the double-line 18. The atmosphere within the room or heat chamber 18' defined by the casing 18, is thermostatically controlled, 19 denoting a thermostat. Within the thermostatically controlled furnace 18,18' the following takes place:

The ions of the liquid sample are separated due to electrical charge of the surface of the respective separator columns 10a, 10b and 10c, respectively. In the examplary embodiment shown, the liquid sample analyser comprises three separator columns 10a–10c, of which a first 10a may be intended for anions, a second 10b for monovalent cations, and a third 10c for divalent cations.

The valve 11 between the separator columns 10a–10c and the detector 13 determines the flow of liquid at all times.

Only one detector 13 and one data acquisition unit 17 are needed in order to operate the entire system. The computer 16 comprises chromatography software and is adapted to control the valves, the polarity of the detector 13 as well as adjusting the latter to zero.

The liquid sample to be analysed is injected from below through the injection port 20 of the pipe line 6,6' and arrives at the three various valve zones 5a–5c almost simultaneously, time differences being of no importance since each injection valve 5a, 5b and 5c, respectively, is formed with a liquid sample accommodation loop closable at both ends and adapted to be closed as soon as it has been filled with liquid sample. Thus, each separator column is supplied with a predetermined extremely accurately measured amount of liquid sample admixed into the respective mobile phase reagent agent from the associated injection valve 5a–5c. However, it is possible to design and adapt the injection valves 5a–5c or possibly the liquid sample supply pipeline 6 in a different way in order to secure the desired dosage of liquid sample to each injection valve.

I claim:

1. A liquid sample analyzer, comprising:
   a plurality of mobile phase containers containing different reagents to be added separately to a common liquid sample;

means for causing each of said different reagents to flow from mobile phase containers to separate pipelines of a pipeline circuit;

a liquid sample injection pipeline having multiple outlets for delivery of said common liquid sample to said separate pipelines of said pipeline circuit;

injection valves adapted to receive one of said separate pipelines containing one of said reagents and one of said outlets from said liquid sample injection pipeline, whereby said reagents and said liquid sample are mixed;

a plurality of ion chromatography separating columns, each of said ion chromatography separating columns attached to one of said injection valves so as to receive the mixed liquid sample and reagent;

means for detecting data from said ion chromatography separating columns;

means for recording said detected data; and a casing to enclose said injection valves and said ion chromatography separating columns.

2. The liquid sample analyser according to claim 1, wherein the ion chromatography separating columns have an upstream preseparating column means.

3. The liquid sample analyzer as set forth in claim 1, wherein said means for recording data is connected to a computer having ion chromatography software, said software adapted to control means which can control said valves.

4. The liquid sample analyzer as set forth in claim 1, wherein said common liquid sample injection pipeline is connected to sensor means for measuring an electrical conductivity and a pH-value of said liquid sample, said sensor means being enclosed within said casing.

* * * * *